United States Patent
Buchdunger et al.

(10) Patent No.: US 6,958,335 B2
(45) Date of Patent: Oct. 25, 2005

(54) TREATMENT OF GASTROINTESTINAL STROMAL TUMORS

(75) Inventors: Elisabeth Buchdunger, Neuenburg (DE); Renaud Capdeville, Riedesheim (FR); George Daniel Demetri, Brookline, MA (US); Sasa Dimitrijevic, Habsheim (FR); Brian Jay Druker, Portland, OR (US); Jonathan A. Fletcher, Brookline, MA (US); Michael C. Heinrich, Lake Oswego, OR (US); Heikki Joensuu, Helsinki (FI); Sandra Leta Silberman, Randolph, NJ (US); David Tuveson, Berwyn, PA (US)

(73) Assignees: Novartis AG, Basel (CH); Dana-Farber Cancer Institute, Inc., Boston, MA (US); Oregon Health & Science University, Portland, OR (US)

(*) Notice: Subject to any disclaimer, the term of this patent is extended or adjusted under 35 U.S.C. 154(b) by 53 days.

(21) Appl. No.: 10/415,015
(22) PCT Filed: Oct. 26, 2001
(86) PCT No.: PCT/EP01/12442
  § 371 (c)(1),
  (2), (4) Date: Aug. 11, 2003
(87) PCT Pub. No.: WO02/34727
  PCT Pub. Date: May 2, 2002
(65) Prior Publication Data
  US 2004/0023976 A1 Feb. 5, 2004

Related U.S. Application Data
(60) Provisional application No. 60/243,810, filed on Oct. 27, 2000.

(51) Int. Cl.$^7$ .............................................. A61K 31/497
(52) U.S. Cl. .................................................... 514/252.18
(58) Field of Search .................................... 514/252.18

(56) References Cited

PUBLICATIONS

Buchdunger et al., Cancer Research, vol. 56, No. 1, (1996), pp. 100–104.*

* cited by examiner

Primary Examiner—Raymond Henley, III
Assistant Examiner—C. Delacroix-Muirheid
(74) Attorney, Agent, or Firm—Oona A. Jackson

(57) ABSTRACT

4-(4-methylpiperazin-1-ylmethyl)-N-[4-methyl-3-(4-pyridin-3-yl)pyrimidin-2-ylamino)phenyl]-benzamide of the formula I

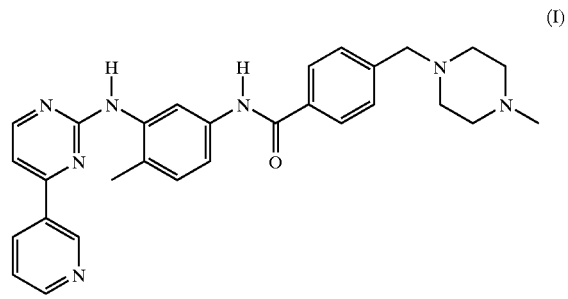

(I)

or a pharmaceutically acceptable salt thereof can be used in the treatment of gastrointestinal stromal tumours.

6 Claims, No Drawings

TREATMENT OF GASTROINTESTINAL STROMAL TUMORS

This application claims the benefit of provisional application Ser. No. 60/243,810 filed Oct. 27, 2000.

The invention relates to the use of 4-(4-methylpiperazin-1-ylmethyl)-N-[4-methyl-3-(4-pyridin-3-yl)pyrimidin-2-ylamino)phenyl]-benzamide (hereinafter: "COMPOUND I") or a pharmaceutically acceptable salt thereof for the manufacture of pharmaceutical compositions for use in the treatment of gastrointestinal stromal tumours (GIST), to the use of COMPOUND I or a pharmaceutically acceptable salt thereof in the treatment of GIST, and to a method of treating warm-blooded animals including humans suffering from GIST by administering to a said animal in need of such treatment an effective dose of COMPOUND I or a pharmaceutically acceptable salt thereof.

Gastrointestinal stromal tumours (GISTs) are a recently characterized family of mesenchymal neoplasms, which originate from the gastrointestinal tract, most commonly from the stomach (60 to 70% of all GISTs). In the past, these tumours were variously classified as leiomyoma, leiomyoblastoma, or leiomyosarcoma. However, it is now clear that GISTs represent a distinct clinicopathologic set of diseases based on their unique molecular pathogenesis and clinical features. GISTs occur most commonly in the middle-aged or elderly with a median age of 50 to 60 years at presentation, and show no significant sex difference in the incidence. It is estimated that at least 10–30% of GISTs are malignant giving rise to intra-abdominal spread and metastases, which are most commonly found in the liver and peritoneal seeding. Malignant GISTs occur at an annual frequency of about 0.3 new cases per 100.000. The most common presenting symptom is vague upper abdominal pain. Many (30%) are asymptomatic, and GISTs may be diagnosed during the evaluation of anaemia resulting from tumour-associated gastrointestinal bleeding.

Management of metastatic and inoperable GIST is a major problem, since GISTs are notoriously unresponsive to cancer chemotherapy. For example, in one recent phase II series, 12 out of 18 (67%) patients with advanced leiomyosarcomas responded to a regimen consisting of dacarbazine, mitomycin, doxorubicin, cisplatin, and sargramostim, but only one (5%) out of 21 GISTs responded (J. Edmonson, R. Marks, J. Buckner, M. Mahoney, Proc. Am. Soc. Clin. Oncol. 1999; 18: 541a "Contrast of response to D-MAP+ sargramostin between patients with advanced malignant gastrointestinal stromal tumors and patients with other advanced leiomyosarcomas"). Treatment results have remained equally unimpressive with other chemotherapy regimens. In line with clinical chemoresistence, expression of P-glycoprotein and multidrug resistance protein MRP1 that associate with multidrug resistance (MDR) are more pronounced in malignant GISTs as compared with leiomyosarcomas.

It has now surprisingly been demonstrated that GIST can be successfully treated with COMPOUND I or pharmaceutically acceptable salt thereof.

COMPOUND I is 4-(4-methylpiperazin-1-ylmethyl)-N-[4-methyl-3-(4-pyridin-3-yl)pyrimidin-2-ylamino)phenyl]-benzamide having the formula I

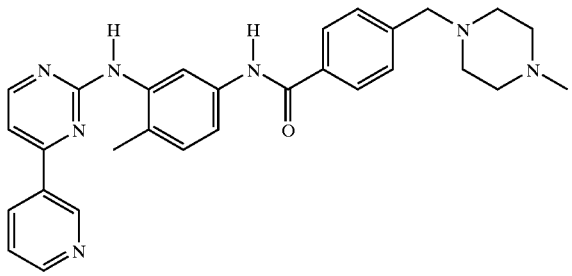

The preparation of COMPOUND I and the use thereof, especially as an anti-tumour agent, are described in Example 21 of European patent application EP-A-0 564 409, which was published on 6 Oct. 1993, and in equivalent applications and patents in numerous other countries, e.g. in U.S. Pat. No. 5,521,184 and in Japanese patent 2706682.

Pharmaceutically acceptable salts of COMPOUND I are pharmaceutically acceptable acid addition salts, like for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid.

The monomethanesulfonic acid addition salt of COMPOUND I (hereinafter "SALT I") and a preferred crystal form thereof are described in PCT patent application WO99/03854 published on Jan. 28, 1999.

In the following treatment results of the first solid tumour patient with unresectable metastatic GIST treated with SALT I are described. The patient had chemotherapy resistant and rapidly progressive metastatic GIST with no therapeutic options other than participation in a clinical trial. The patient had documented rapid progression of chemotherapy resistant GIST in multiple sites. SALT I was given orally at the dose of 400 mg daily. Treatment effect was evaluated longitudinally with imaging studies [including dynamic magnetic resonance imaging (MRI) and positron emission tomography (PET) using $^{18}$F-fluorodeoxy-glucose as the tracer]; in addition, serial biopsies of metastatic tumour from liver were evaluated for evidence of histopathologic effect of SALT I.

A complete metabolic response in tumour with negative PET imaging was achieved within 1 month after starting treatment with SALT I, when the tumour volume had decreased by 52% in magnetic resonance imaging (MRI), i.e. a 52% reduction in the total volume of liver metastases was achieved within 1 month after starting treatment with SALT I based on MRI. Many liver metastases became cystic, and dynamic MRI showed markedly reduced tumour enhancement suggesting decreased tumour viability. Moreover, histopathologic evaluation obtained by serial biopsies of the tumour confirmed the anticancer activity of this treatment. The PET scan revealed that $^{18}$F-fluorodeoxyglucose (FDG) high avidity uptake by tumour was negative within 1 month of treatment with SALT I. The pattern of contrast enhancement of tumour by dynamic MRI decreased dramatically within 2 weeks after starting SALT I, and many of the metastatic lesions became cystic during follow-up. The malignant GIST tissue was replaced by fibrosis and necrosis in serial needle biopsies. With continued treatment, gradual shrinkage in the size of the liver lesions occurred, and hypometabolic areas were noted in place of hypermetabolic liver metastases in PET. These findings suggest that the persisting residual liver lesions visible on MRI scans likely contain little or no viable disease. These beneficial clinical and imaging responses have been documented for 7 months on treatment.

Importantly, the clinical toxicity profile of oral SALT I therapy was remarkably favourable, consisting mainly of mild cytopenias and slightly increased frequency of bowel movements.

Depending on species, age, individual condition, mode of administration, and the clinical picture in question, effective doses, for example daily doses of about 100–1000 mg, preferably 200–600 mg, especially 400 mg, are administered to warm-blooded animals of about 70 kg bodyweight. For adult patients with unresectable and/or metastatic malignant GIST, a starting dose of 400 mg daily can be recommended. For patients with an inadequate response after an assessment of response to therapy with 400 mg daily, dose escalation can be safely considered and patients may be treated as long as they benefit from treatment and in the absence of limiting toxicities.

The invention relates also to a method for administering to a human subject having GIST COMPOUND I or a pharmaceutically acceptable salt thereof, which comprises administering a pharmaceutically effective amount of COMPOUND I or a pharmaceutically acceptable salt thereof to the human subject once daily for a period exceeding 3 months. The invention relates especially to such method wherein a daily dose of 200 to 600 mg, especially 400–600 mg, preferably 400 mg, of SALT I is administered.

EXAMPLE 1

A) Case History

A 50-year-old previously healthy Caucasian female presented with mild abdominal discomfort and a large tumour in the upper abdomen in October 1996. Two tumours, 6.5 and 10 cm in diameter, were removed from the stomach using proximal gastric resection, and the greater omentum and the mesocolic peritoneum were removed due to multiple metastatic nodules 1 to 2 mm in size. Tumour histology was compatible with malignant GIST with over 20 mitoses per 10 high power fields. A recurrent tumour in the left upper abdomen, 2 liver metastases, and multiple small intra-abdominal metastases were excised in February 1998, and in September 1998 six further liver metastases and an ovary metastasis were removed. Seven cycles of IADIC (ifosfamide, doxoribicin, and dacarbazine) were given from November 1998 to March 1999 for multiple liver metastases. No response to IADIC was obtained, and a large bowel-obstructing metastasis and 45 smaller metastases were removed at laparotomy in March 1999. She was subsequently treated between April 1999 and February 2000 with an experimental regimen consisting of thalidomide 400 mg once daily and interferon alpha 0.9 MU T.I.D. s.c. to control persisting liver disease. Following 6-month disease stabilization liver metastases progressed rapidly and several new metastases appeared, and in February 2000 28 liver metastases and at least 2 metastases in the upper abdomen were found in MRI, causing compression of the portal and hepatic veins.

Treatment with SALT I at the dose of 400 mg (4 capsules as described in Example 2) once daily orally was started in March 2000.

B) Assessment of Treatment Toxicity and Response

Treatment toxicity was assessed at follow-up visits performed at 2 to 4 week intervals, and blood cell counts and blood chemistry were analysed at 1 to 2 week intervals. Treatment response was assessed with dynamic MRI scans, $^{18}$F-fluorodeoxyglucose (FDG) positron emission tomography (PET) examinations, and cutting needle biopsies from a liver metastasis. Dynamic MRI was performed with a 1.5T Magnetom Vision (Siemens, Erlangen, Germany). Fat-suppressed T1-weighted breathhold gradient echo transaxial images were obtained both before and after intravenous contrast medium injection (0.1 mmol/kg gadolinium-DOTA; Dotarem, Guerbet, France). The enhancement pattern was established using sequential imaging over 5 minutes, and delayed scanning was performed after 10 minutes. FDG PET was done using an 8-ring ECAT 931/08 device (Siemens-CTI Corp. Knoxville, Tenn.). The FDG dose given varied between 355 to 375 MBq.

C) Results

Tumour Response in MRI

A considerable reduction in the patient's total tumour size was achieved within weeks after SALT I treatment. The tumour area (measured as the sum of the products of 2 bi-perpendicular parameters) of 8 large measurable liver metastases was 112.5 cm$^2$ in an MRI scan performed 1 day before starting SALT I. In follow-up MRI scans performed while SALT I treatment was ongoing, the total tumour size decreased to 66.9 cm$^2$ by 2 weeks after starting SALT I (a decrease of 41%), to 54.3 cm$^2$ at 1 month (52% decrease), to 41.5 cm$^2$ at 2 months (63% decrease), to 36.2 cm$^2$ at 4 months (68% decrease), and to 32.5 cm$^2$ at 5.5 months (71% decrease) on treatment. No new lesions appeared, and 6 of the 28 liver metastases disappeared. The peripheral rim of metastases that showed considerable contrast enhancement by dynamic MRI (consistent with viable tumour) before starting SALT I showed dramatic reduction of this finding, with little or no enhancement in dynamic MRIs taken during treatment, and many metastases became cystic. In September 2000 the tumour continued to respond and the patient remained clinically well.

Imaging by Positron Emission Tomography (PET Scanning)

A remarkable change was seen in serial FDG PET images of the tumours, suggestive of anti-tumour metabolic response. Multiple liver metastases and accumulation of FDG to the right kidney compatible with hydronephrosis was seen in a PET scan taken 4 days before starting SALT I. In a repeat PET taken 1 month after starting SALT I, no abnormal FDG uptake was present in the liver, and the right kidney showed normal uptake. Consistent with the induction of cystic changes in metastases seen in MRI and necrosis in needle biopsies, "cold" areas showing less FGD uptake than the surrounding liver parenchyma were seen at the sites of liver metastases in a PET taken 2 months after starting SALT I.

Histological Response

Serial cutting needle biopsies taken from a ventrally located liver metastases 1 and 2 months after starting SALT I showed marked decrease in GIST cell density, and myxoid degeneration and scarring with no signs of overt inflammatory reaction or necrosis.

Tolerability of SALT I Treatment

Treatment with SALT I was well tolerated overall. No hair loss was observed, and the patient reported only mild occasional nausea related to swallowing of the drug capsules, lasting for about 15 minutes improved after taking drug with food. Blood cell count changes were unremarkable. Her blood haemoglobin level varied between 118 g/L and 125 g/L during SALT I therapy (the pretreatment value was 120 g/L), the white blood cell count from 3.2 to $4.4 \times 10^9$/L ($5.5 \times 10^9$/L), the granulocyte count from 1.52 to $2.39 \times 10^9$/L ($3.2 \times 10^9$/L), and the platelet count from 261 to $365 \times 10^9$/L ($360 \times 10^9$/L). No drug-related liver, renal or cardiac toxicity was observed. The main subjective toxicity [all Grade 1 (NCI CTC version 2.0)] consisted of increased frequency of bowel movements (2 to 4 times a day), occasional muscle cramps in the legs, slight transient ankle oedema, and a Herpes zoster infection with rash located on the left ventral (LV) dermatome was diagnosed during SALT I therapy. The World Health Organization (WHO) performance status improved from 1 (cancer related symptoms present) to 0 (normal) during SALT I therapy.

EXAMPLE 2

Capsules with 4-[(4-methyl-1-piperazin-1-ylmethyl)-N-[4-methyl-3-[[4-(3-pyridinyl)-2-pyrimidinyl]amino]phenyl]benzamide methanesulfonate, β-crystal form Capsules containing 119.5 mg of the compound named in the title (=SALT I) corresponding to 100 mg of COMPOUND I (free base) as active substance are prepared in the following composition:

| Composition | |
|---|---|
| SALT I | 119.5 mg |
| Cellulose MK GR | 92 mg |
| Crospovidone XL | 15 mg |
| Aerosil 200 | 2 mg |
| Magnesium stearate | 1.5 mg |
| | 230 mg |

The capsules are prepared by mixing the components and filling the mixture into hard gelatin capsules, size 1.

EXAMPLE 3

Capsules with 4-[(4-methyl-1-piperazin-1-ylmethyl)-N-[4-methyl-3-[[4-(3-pyridinyl)-2-pyrimidinyl]amino]phenyl]benzamide methanesulfonate, β-crystal form Capsules containing 100 mg of the compound named in the title (=SALT I) as active substance are prepared in the following composition:

| Composition | |
|---|---|
| Active substance | 100 mg |
| Avicel | 200 mg |
| PVPPXL | 15 mg |
| Aerosil | 2 mg |
| Magnesium stearate | 1.5 mg |
| | 318.5 mg |

The capsules are prepared by mixing the components and filling the mixture into hard gelatin capsules, size 1.

EXAMPLE 4

At the priority date of the present patent application a clinical study with more GIST patients was being conducted analogously to the study described in Example 1. The study was not yet finished, but it could be already stated that from 33 evaluable patients 6 patients had not yet been evaluated and that from the remaining 27 patients only 1 patient showed progression of the disease, 18 patients had stable disease, i.e. 4–42% reduction, and 8 patients showed partial response, i.e. 50–66% reduction.

EXAMPLE 5

A phase 2, open-label, randomized multinational study was conducted in patients with unresectable and/or metastatic malignant gastrointestinal stromal tumors (GIST). In this study 147 patients were enrolled and randomized to receive either 400 mg or 600 mg of SALT I orally once daily for up to 24 months. These patients ranged in age from 18 to 83 years old and had a pathologic diagnosis of CD 117-positive, unresectable and/or metastatic malignant GIST. The primary evidence of efficacy was based on objective response rates, and the time to response, duration of response, time to treatment failure and survival were also evaluated. Tumors were required to be measurable in at least one site of disease, and response characterization based on Southwestern Oncology Group (SWOG) criteria. Results are derived from an interim analysis of this study and summarized in the following table:

| | Best tumor response | | |
|---|---|---|---|
| Best response | 400 mg (N = 73) n (%) | 600 mg (N = 74) n (%) | All doses (N = 147) n (%) |
| Complete response | 0 | 0 | 0 |
| Partial response | 27 (37.0) | 32 (43.2) | 59 (40.1) |
| Stable disease | 33 (45.2) | 28 (37.8) | 61 (41.5) |
| Progressive disease | 10 (13.7) | 8 (10.8) | 18 (12.2) |
| Not evaluable | 3 (4.1) | 4 (5.4) | 7 (4.8) |
| Unknown | 0 | 2 (2.7) | 2 (1.4) |

Due to the limited follow-up of patients, and the significant number of patients with stable disease at the time of the interim analysis which was made about one year after start of the trial, this group was evaluated further. Among the 61 patients with "stable disease", significant tumor shrinkage was seen in 47 patients, with either a partial response not yet confirmed by a second assessment (28 patients) or a reduction in the size of their tumor by more than 25% (19 patients). The number of responders may, therefore, increase in the future with confirmation or attainment of a partial response after these patients have been exposed to SALT I for a longer period of time.

Altogether, a total of 118 patients (80%) had a reduction in the size of their tumor by more than 25% on at least one assessment. These patients include those who had a confirmed (n=59) and an unconfirmed (n=28) partial response, a confirmed stable disease with more than 25% reduction (n=19), and twelve other patients who had a reduction of tumor size of more than 25% at any tumor assessment. No patients with confirmed response had relapsed.

The median time to the onset of response was 12 weeks for the entire study population. The duration of response observed at the time of the interim analysis (no interval censoring) ranged from seven to 38 weeks, with a median of approximately 14 weeks.

An estimate of the number of patients free from treatment failure at 12 weeks was 80%, and this estimate was 66% at 24 weeks. Without interval-censoring, the estimates were 81% and 67%, respectively. Median time to treatment failure (interval censoring) was 54 weeks in the pooled population (all treated patients), however, this estimate was based on only two patients and thus is not a reliable estimate.

Overall survival was not statistically analyzed due to the small number of deaths observed and the relatively short follow-up period.

Differences between dose groups could not be observed in any of the efficacy parameters evaluated.

What is claimed is:

1. A method of treating gastrointestinal stromal tumours which comprises administering to a human in need of such treatment a dose, effective against gastrointestinal stromal tumours, of 4-(4-methylpiperazin-1-ylmethyl)-N-[4-methyl-3-(4-pyridin-3-yl)pyrimidin-2-ylamino)phenyl]-benzamide of the formula I

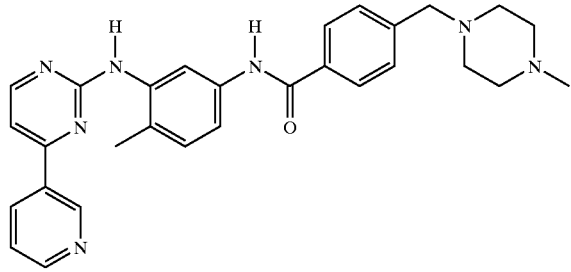

(I)

or a pharmaceutically acceptable salt thereof.

2. The method according to claim 1 wherein a pharmaceutically acceptable acid addition salt of 4-(4-methylpiperazin-1-ylmethyl)-N-[4-methyl-3-(4-pyridin-3-yl)pyrimidin-2-yl-amino)phenyl]-benzamide of the formula I is administered.

3. The method according to claim 1 wherein a methanesulfonate salt of 4-(4-methylpiperazin-1-ylmethyl)-N-[4-methyl-3-(4-pyridin-3-yl)pyrimidin-2-ylamino)phenyl]-benzamide of the formula I is administered.

4. The method according to claim 1 wherein a daily dose of 200 to 600 mg of a monomethanesulfonate salt of 4-(4-methylpiperazin-1-ylmethyl)-N-[4-methyl-3-(4-pyridin-3-yl)pyrimidin-2-ylamino)phenyl]-benzamide of the formula I is administered to an adult human.

5. A method for administering to a human subject having gastrointestinal stromal tumours 4-(4-methylpiperazin-1-ylmethyl)-N-[4-methyl-3-(4-pyrimidin-3-yl)pyrimidin-2-ylamino)phenyl]-benzamide of the formula I

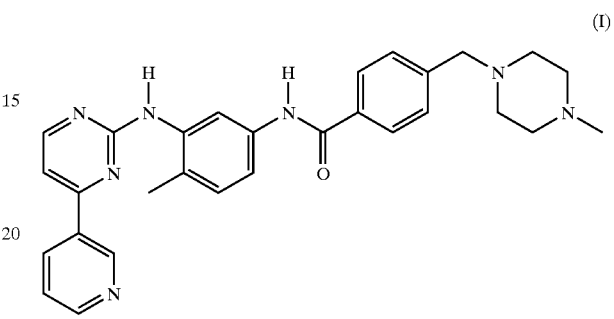

(I)

or a pharmaceutically acceptable salt thereof, which comprises administering a pharmaceutically effective amount of 4-(4-methylpiperazin-1-ylmethyl)-N-[4-methyl-3-(4-pyridin-3-yl)pyrimidin-2-ylamino)phenyl]-benzamide of the formula I or a pharmaceutically acceptable salt thereof to the human subject once daily for a period exceeding 3 months.

6. A method according to claim 5 wherein a daily dose of 200 to 600 mg of monomethanesulfonate salt of 4-(4-methylpiperazin-1-ylmethyl)-N-[4-methyl-3-(4-pyridin-3-yl)pyrimidin-2-ylamino)phenyl]-benzamide of the formula I is administered.

* * * * *